United States Patent [19]

Hodge

[11] 4,409,392
[45] Oct. 11, 1983

[54] 6' ESTERS OF ZEARALANOL

[75] Inventor: Edward B. Hodge, Terre Haute, Ind.

[73] Assignee: International Minerals & Chemical Corp., Terre Haute, Ind.

[21] Appl. No.: 299,271

[22] Filed: Sep. 3, 1981

[51] Int. Cl.$^3$ ............................................. C07D 313/00
[52] U.S. Cl. ..................................... 549/270; 424/279
[58] Field of Search ..................... 260/343.41; 549/270

[56] References Cited

U.S. PATENT DOCUMENTS

| | | | |
|---|---|---|---|
| 3,196,019 | 7/1965 | Andrews et al. | 424/279 |
| 3,239,341 | 3/1966 | Hodge et al. | 424/279 |
| 3,239,345 | 3/1966 | Hodge et al. | 424/279 |
| 3,239,356 | 3/1966 | Hodge et al. | 260/343.41 |
| 3,373,037 | 3/1968 | Abbott | 260/343.41 |
| 3,373,038 | 3/1968 | Hodge et al. | 260/343.41 |
| 3,373,039 | 3/1968 | Hodge et al. | 260/343.41 |
| 3,687,982 | 8/1972 | Young | 260/343.41 |
| 3,887,583 | 6/1975 | Wehrmeister et al. | 260/343.41 |
| 4,062,970 | 12/1977 | Shipchandler | 260/343.41 |

OTHER PUBLICATIONS

Hidy, P. H. et al.: "Zearalenone and Some Derivatives: Production and Biological Activities", Adv. Appl. Microbiol. 22:59-82, 1977.

Primary Examiner—Jane T. Fan
Attorney, Agent, or Firm—Steven R. Lammert; H. J. Barnett

[57] ABSTRACT

Novel compositions of matter comprising the 6' esters of zearalanol which have utility as growth promoting agents in meat-producing animals, particularly ruminants. The compositions include: zearalanol 6'-butyrate; zearalanol 6'-decanoate; zearalanol 6'-hexanoate; zearalanol 6'-laurate; zearalanol 6'-trichloroacetate; and zearalanol 6'-trifluoroacetate.

1 Claim, No Drawings

6' ESTERS OF ZEARALANOL

BACKGROUND

There is increasing need for anabolic substances for promoting growth in meat-producing animals. A number of macrolide compositions of the general group known as resorcyclic acid lactones (RAL's) and their derivatives exhibit some level of anabolic activity. It is important that the compositions to be used have the highest possible level of growth promoting activity with no harmful side effects.

PRIOR ART

A number of resorcyclic acid lactone derivatives are described by P. H. Hidy et al in a publication entitled "Zearalenone and Some Derivatives: Production and Biological Activities", *Adv. Appl. Microbiol.* 22:59-82, 1977. Zearalenone exhibits anabolic properties when administered to certain animal species. Some of its related derivatives, particularly zearalanone (M.P. 192°–193° C.) and zearalanol (M.P. 178°–180° C.), possess significant anabolic properties. Zearalenone (164°–165° C.) is described in U.S. Pat. No. 3,196,019. Reduction of the olefinic group of zearalenone following the reduction procedure set forth in U.S. Pat. No. 3,239,341, by hydrogenation in the presence of a palladium catalyst, will produce zearalanone (M.P. 192°–193° C.), and complete reduction as disclosed in U.S. Pat. No. 3,239,345 will produce zearalanol (M.P. 178°–180° C.).

SUMMARY

This invention is directed to a group of novel ester derivatives of zearalanol which are useful as anabolic agents when administered to meat-producing animals, particularly ruminants such as cattle and sheep. These novel ester derivatives include zearalanol 6'-butyrates; zearalanol 6'-decanoate; zearalanol 6'-hexanoate; zearalanol 6'-laurate; zearalanol 6'-trichloroacetate; and 6'-trifluoroacetate; and are usually administered as a subcutaneous implant.

A general structural formula for these compositions is set forth below:

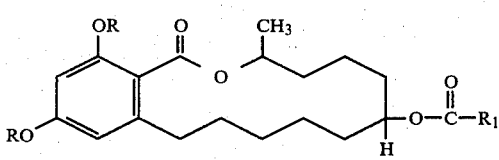

in which R=hydrogen; alkyl; aryl; carboxylic acyl; or aralkyl, the R groups being the same or different; $R_1$=alkyl or aryl or substituted alkyl or aryl, including trichloroalkyl and trifluoroalkyl.

DETAILED DESCRIPTION

EXAMPLE 1

Preparation of Zearalanol 6'-Hexanoate

Three parts of zearalanol (M.P. 178°–180° C.) were mixed in fifty parts dry acetone, 2 parts dimethylformamide and 1.5 parts hexanoyl chloride. The mixture was allowed to react at ambient temperature (65°–75° F.) until the analysis showed that a reaction had taken place. The reaction mixture was added to 700 parts ice water, stirred for thirty minutes, and then filtered. The resulting precipitate was air-dried for about one hour, and then extracted with boiling cyclohexane.

Filtration of the extracted precipitate yielded a precipitate of 1.3 parts unreacted zearalanol. The filtrate from the preceding step was then cooled to about 23° C., and again filtered to collect a precipitate of 1.5 parts zearalanol 6'-hexanoate, M. P. 104°–110° C. of the following structural formula:

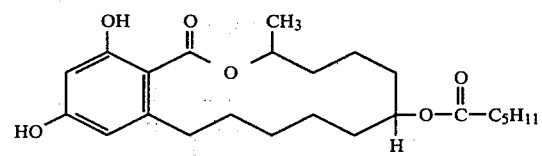

Molecular Weight: 420.53

EXAMPLE 2

The above synthesis was repeated with all proportions and reagents and conditions being the same, except that one part of dimethylformamide was used instead of two parts. The yield of zearalanol 6'-hexanoate, M.P. 104°–110° C. was increased.

EXAMPLE 3

Three parts of zearalanol (M.P. 178°–180° C.) were mixed in fifty parts dry acetone. Five parts unpowdered molecular sieve (Davison Type 5A, Grade 522) and 1.5 parts hexanoyl chloride were then added, and the reaction mixture was allowed to stand until the reaction was complete. The reaction mixture was then filtered, the filtrate was mixed with 700 parts cold water and stirred for twenty minutes, and filtered again. The precipitate from the last filtration step was dried for three hours, boiled with sixty parts cyclohexane and filtered hot to remove 0.3 parts unreacted zearalanol. The resulting filtrate was cooled to about 20° C., and after about twenty minutes at the lower temperature, it was filtered again to produce a precipitate of about 2.6 parts zearalanol 6'-hexanoate, M.P. 111°–114° C.

EXAMPLE 4

Preparation of Zearalanol 6'-Decanoate

Fifty parts acetone, 3.8 parts decanoyl chloride and 6 parts zearalanol (M.P. 178°–180° C.) were mixed together and refluxed for about five and one-half hours, and then evaporated. The residue was redissolved in sixty parts cyclohexane, concentrated to about thirty parts, and about sixty parts n-hexane was added to the mixture. The mixture was then stirred for about thirty minutes and filtered to produce about 3.5 parts zearalanol 6'-decanoate, M.P. 86°–89° C. The structural formula for this ester is:

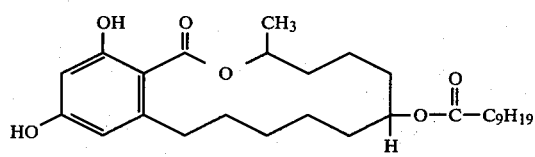

Molecular Weight: 473.6

EXAMPLE 5

Preparation of Zearalanol 6'-Butyrate

The procedure set forth above in Example 4 can be followed to produce zearalanol 6'-butyrate by substituting butanoyl chloride for decanoyl chloride, otherwise, the steps are substantially the same. Zearalanol 6-'-butyrate (M.P. 162°–165° C.) is produced. The structural formula for this ester is:

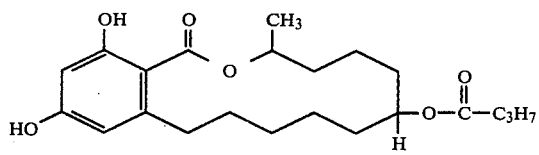

Molecular Weight: 397.5

EXAMPLE 6

Preparation of Zearalanol 6'-Laurate

The procedure set forth above in Example 4 is again followed to produce zearalanol 6'-laurate by substituting lauranoyl chloride for decanoyl chloride, otherwise, the steps are substantially the same. Zearalanol 6'-laurate (M.P. 85°–86° C.) is obtained. The structural formula is:

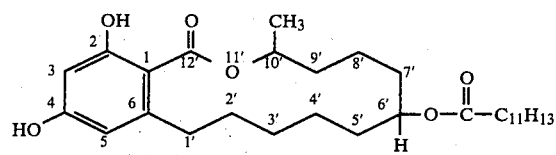

Molecular Weight: 504.7

EXAMPLE 7

Preparation of Zearalanol 6'-Trichloroacetate

Six parts of zearalanol (M.P. 178°–180° C.) is first refluxed with 4.3 parts trichloroacetyl chloride in 50 parts acetone for about 4¼ hours. The reaction mixture was then stirred in 300 parts cold water. The precipitate was recrystallized from cyclohexane to yield 3.7 parts of zearalanol 6'-trichloroacetate (M.P. 129°–132° C.) having a structural formula as set forth below:

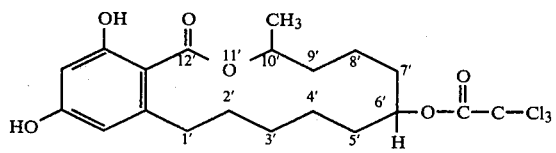

Molecular Weight: 467.78

It is also contemplated that the 6'-tribromoacetate esters of zearalanol can be made following the above general procedure, but using tribromoacetylchloride or bromide.

EXAMPLE 8

Preparation of Zearalanol 6'-Trifluoroacetate

To 75 parts of methylene chloride was added 3.0 parts of zearalanol and 2 parts of trifluoroacetic anhydride. The mixture was warmed for three minutes while the zearalanol dissolved. The solvent was then evaporated and the residue was recrystallized from 120 parts of cyclohexane to give 2 parts of zearalanol 6'-trifluoroacetate (M.P. 118°–121° C.).

EXAMPLE 9

Preparation of 6'-Zearalanol p-Nitrobenzoate

Twelve parts of zearalanol (M.P. 178°'180° C.) is first mixed with nine parts of p-nitrobenzoyl chloride in 150 parts of toluene and refluxed for about fourteen hours. After cooling and filtering, there were eleven parts of material which melted at 148°–155° C. This material was recrystallized from 75 parts of 2-nitropropane, and then from 50 parts toluene to yield 3.7 parts of 6'-zearalanol p-nitrobenzoate (M.P. 156°–158° C.). The structural formula for this compound is set forth below:

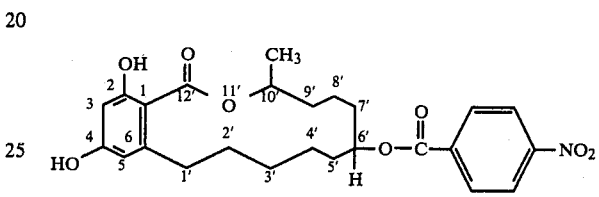

Molecular Weight: 471.49

EXAMPLE 10

Preparation of 6'-Zearalanol p-Aminobenzoate

The composition prepared in the preceding example can be subjected to a reduction reaction to reduce the nitrobenzoate group to aminobenzoate, as set forth below.

Three parts of 6'-zearalanol p-nitrobenzoate (M.P. 156°–158° C.) produced by the method of the preceding example is mixed with 150 parts ethanol and one part 5% palladium catalyst plus 2 parts water and hydrogenated for four hours. The reaction mixture was filtered and concentrated to about 20 parts, refiltered and the precipitate was dried to yield 1.5 parts 6'-zearalanol p-aminobenzoate.

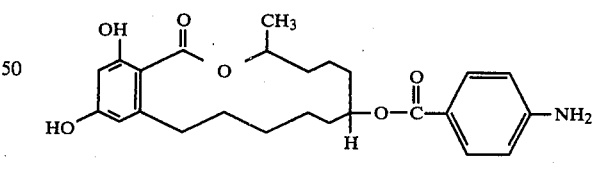

Molecular Weight: 441.49 (calc)

EXAMPLE 11

Preparation of Zearalanol 6'-Succinate

Six parts of zearalanol (M.P. 178°–180° C.) was refluxed in 60 parts acetone with 1 part succinyl chloride for about five hours and then cooled. A precipitate was formed which was filtered and washed, and dissolved in hot acetone and again cooled. This solution formed a precipitate which was filtered to recover 1.2 parts of zearalanol 6'-succinate (M.P. 163°–165° C.). The structural formula for this product is:

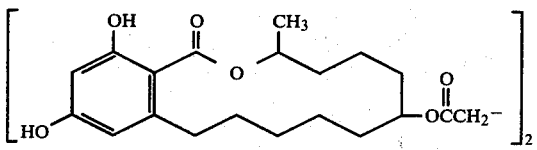

Molecular Weight: 726.83

EXAMPLE 12

Effect of Zearalanol 6'-Hexanoate on Nitrogen Metabolism of Lambs

The compound of Example 1 above was tested for anabolic activity in ruminants. Twelve Columbia wether lambs, previously adapted to a completely ground ration were acclimated in metabolism cages for ten days. The lambs were offered food ad libitum to a maximum of 1.4 kg per hread per day. Water was continuously available. The subject compound was prepared and administered as a subcutaneous implant, and compared to a positive control implant which contained zeranol, a known effective anabolic agent, and to a control which received only the ration set forth in Table 1 below.

TABLE 1

| Composition of the Basal Ration | | |
|---|---|---|
| Item | International Reference No. | Percent |
| Corn, cracked shelled | 4-02-931 | 68.7 |
| Alfalfa-whole corn plant, dehydrated[a] | | 20.0 |
| Soybean meal (44%) | 5-20-637 | 7.5 |
| Cane molasses | 4-04-696 | 2.0 |
| Limestone | 6-02-632 | 0.8 |
| Trace mineral salt[b] | | 0.6 |
| Vitamin premix[c] | | 0.4 |
| Calculated composition (as fed basis) | | |
| Crude protein | | 11.9 |
| Crude fiber | | 6.8 |
| Calcium | | 0.48 |
| Phosphorus | | 0.28 |
| Potassium | | 0.73 |
| Sulfur | | 0.27 |
| Digestable energy | | 3.08 Mcal/kg |

[a]Charles H. Schenk and Sons, Inc., Vincennes, Indiana. Guaranteed analysis: crude protein, min. 12.00%; crude fiber, max. 25.00%; fat, min. 1.50%; calcium, min. 0.75%, max 0.87%; and phosphorus, min. 0.20%.
[b]Composition: NaCl, not >99.0%, not <95.0%; and not <0.35% Zn, 0.34% Fe, 0.200% Mn, 0.033% Cu, 0.077% I, and 0.005% Co.
[c]Provides per kg of diet: 2750 IU vitamin A; 700 IU vitamin D, and 10 IU vitamin E.

The implants were formulated as set forth below in Table 2.

TABLE 2

| Composition of Implants | | | |
|---|---|---|---|
| | Implants | | |
| Component | Placebo | Zearalanol 6'-Hexanoate | Zeranol |
| | mg per implant | | |
| Zearalanol 6'-Hexanoate | — | 12.00 | — |
| Zeranol | — | — | 12.00 |
| Bovine fibrin | 3.35 | 3.35 | 3.35 |
| Magnesium stearate | 0.25 | 0.25 | 0.25 |
| Boric acid | 0.55 | 0.55 | 0.55 |
| Lactose | 12.00 | — | — |
| Total | 16.15 | 16.15 | 16.15 |

The above placebo implants, zeranol and zearalanol 6'-hexanoate implants were repeated in four lambs each. The placebo implants contained 12 mg lactose instead of the experimental compounds.

Urine was collected from all test animals with care taken to prevent contamination. The lambs were fed twice daily at 9:00 A.M. and 3.30 P.M. Orts were removed and weighed daily prior to the morning feeding, composited by lamp and period, and refrigerated until analysis. Continuous lighting was provided.

Kjeldahl nitrogen determinations were made on samples of feed, orts and urine. Urinary area nitrogen was determined by a modification of the diacetyl monoxime method set forth in Crocker, Amer. J. Med. Tech. 33:361 (1967).

Theory

The urinary nitrogen excretion reflects a loss of nitrogen due to absorption of food nitrogen in excess of anabolic needs and/or nitrogen resulting from catabolic activity. By increasing anabolic processes (nmuscle growth, synthesis of plasma proteins, etc.) and/or decreasing catabolic reactions, urinary nitrogen may be decreased provided that food intake remains relatively unchanged. The urinary nitrogen excretion is, therefore, an indicator of whole body nitrogen metabolism. When anabolic activity is increased as is presumably the case in the young growing animal, more amino acids are utilized for protein synthesis and less urea is formed and excreted.

In the subject test, the dietary nitrogen intake for all twelve test animals was not significantly different.

Table 3 below shows the results of the test.

TABLE 3

| Nitrogen Metabolism response Data | | | | |
|---|---|---|---|---|
| | Test | Treatments | | |
| Parameter | Period | Placebo | Zeranol | 6'-Hexanoate |
| | Change relative to control period[a] | | | |
| Nitrogen intake, | 3 | +5.6 | −10.4 | −9.3 |
| g/period | 4 | −2.6 | −4.9 | −4.4 |
| | 3 & 4 | +1.5 | −7.6 | −6.8 |
| Urinary nitrogen | 3[b] | +1.6 | −7.2* | +3.8 |
| total, g/period | 4 | +7.4 | −3.8* | +1.2 |
| | 3 & 4 | +6.4 | −5.0* | +0.1 |
| total, | 3[b] | +0.08 | −0.30* | +0.14 |
| g/BW · $\frac{75}{kg}$/period | 4 | +0.44 | −0.22* | +0.08 |
| | 3 & 4 | +0.38 | −0.28* | +0.01 |
| % of intake | 3 | +11.9 | −1.4 | +9.2 |
| | 4 | +8.3 | −2.1 | +3.2 |
| | 3 & 4 | +5.6 | −1.2 | +2.7 |
| Urinary urea | 3[b] | +7.7 | −1.1* | −1.7* |
| nitrogen, | 4 | +7.3 | −7.5* | +1.9 |
| g/period | 3 & 4 | +7.5 | −4.3* | +0.1* |

*Significantly different from Placebo treatment (P < .05).
[a]Each value is the mean of four animals.
[b]Means adjusted by analysis of co-variance where x = value during control period and y = change in value during test period.

The test was divided into 5-day collection periods. Period 1 was a familiarization period, and Period 2 functioned as a baseline control period. The lambs were implanted at the end of Period 2, and the two test periods 3 and 4 followed. Between each period was a two-day rest period. A single pellet of the appropriate treatment was inmplanted subcutaneously near the base of the ear. The lambs were weighed at the beginning of period 1 and at the end of Period 4.

The results shown in Table 3 show that the 6'-hexanoate ester of zearalanol produced a significant increase in urinary urea nitrogen retention, indicating a significant growth response in the animals treated with the subject 6' ester of zearalanol, compared to the animals receiving only the placebo implant. The change in urinary urea nitrogen during Period 3 and Periods 3 & 4 combined was significantly less for both the test compound (zearalanol 6'-hexanaote) and the positive control (zerand) when compared to the negative control (placebo). Animals implanted with zearalanol 6'-hexanoate underwent little change in urea excretion while the negative control (placebo) lambs substantially increased urinary urea excretion. Supporting data also may be found in the conservation of total urinary nitrogen for the 6'-ester group compared to the placebo group during Period 3 and Periods 3 & 4 combined. The above results confirmed that zearalanol 6'-hexanoate ans its related zeranol esters product an effect similar to that produced by zeranol in ruminant animals, that is, an increase in the anabolic processes. Therefore, it may be concluded that zearalanol 6'-hexanoate and its related compounds are effective as anabolic agents in animals, more particularly, ruminant animals and, specifically, sheep.

I claim:

1. The composition

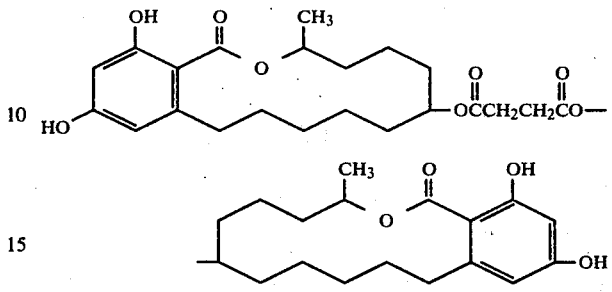

* * * * *